United States Patent [19]

Nakoneczny et al.

[11] Patent Number: 5,242,111

[45] Date of Patent: Sep. 7, 1993

[54] WICK TYPE LIQUID DISPENSING DEVICE FOR THE SLOW CONTROLLED DISPENSING AND DIFFUSION OF LIQUIDS OVER AN EXTENDED PERIOD OF TIME

[76] Inventors: John Nakoneczny; Sharon A. Nakoneczny, both of 5466 Dorothy Dr., North Olmsted, Ohio 44070

[21] Appl. No.: 928,759

[22] Filed: Aug. 13, 1992

[51] Int. Cl.$^5$ ............................................. A61L 9/04
[52] U.S. Cl. ........................................ 239/47; 239/44; 239/55
[58] Field of Search .................. 239/44, 45, 46, 47, 239/48, 49, 50, 51, 55

[56] References Cited

U.S. PATENT DOCUMENTS

| | | | |
|---|---|---|---|
| 2,520,056 | 8/1950 | Pozun | 239/51 |
| 2,747,332 | 5/1956 | Morehouse | 239/44 |
| 3,633,881 | 1/1972 | Yurdin | 239/44 |
| 3,702,677 | 11/1972 | Heffington | 239/47 |
| 4,223,837 | 9/1980 | Gubbiotti | 239/50 |
| 4,606,478 | 8/1986 | Hack et al. | 239/47 |
| 4,970,823 | 11/1990 | Chen et al. | 239/44 |
| 4,971,251 | 11/1990 | Dobrick et al. | 239/600 |
| 5,077,102 | 12/1991 | Chong | 239/44 |

Primary Examiner—Andres Kashnikow
Assistant Examiner—Christopher G. Trainor

[57] ABSTRACT

A liquid dispensing device capable of dispensing an active liquid at a slow substantially constant rate over an extended period of time. The liquid dispenser consists of a sealed flexible bag or pouch containing a supply of the active liquid, a wick located inside a tubular member, and an emanator which diffuses the active liquid. The active liquid supply inside the impermeable bag is kept isolated from the wick prior to use by means of a containment element. Upon removal of the containment member, the active liquid is free to contact the wick, whereby the enclosed tubular wick conveys the active liquid to the emanator for slow dispersion. The sealed reservoir bag gradually collapses inward as the active liquid supply is depleted, obviating the need for a vent. The liquid dispensing device could be used as an air freshener, diffusing a volatile scent-producing liquid into the atmosphere. The device could also be adapted to dispense pharmaceuticals transdermally. In another modification, the device could be used to dispense vegetative nutrients to cultivated soil or into the water of hydroponic vegetation.

20 Claims, 5 Drawing Sheets

WICK TYPE LIQUID DISPENSING DEVICE FOR THE SLOW CONTROLLED DISPENSING AND DIFFUSION OF LIQUIDS OVER AN EXTENDED PERIOD OF TIME

FIELD OF THE INVENTION

The present invention belongs most broadly to the field of liquid dispensing devices, used for the slow controlled dispensing and diffusion of liquids and vaporizable materials. More particularly, the present invention relates to wick type dispensing devices, which employ a wick to convey a liquid or vaporizable material, from an enclosed container by capillary action, to an emanator.

BACKGROUND OF THE INVENTION

Liquid dispensers which employ a wick to convey a liquid or a volatile material from a container to a emanator, are well known in the art. A wide variety of liquid dispensers which are designed to slowly diffuse an active liquid, and which employ a wick, already exist. The active liquid may be a volatile scent-producing liquid, as in the case of air fresheners. In the case of wick type air fresheners, the scent-producing liquid is conveyed from a container, by means of capillary action through a wick, to an emanator, which diffuses the scent-producing liquid into the atmosphere in the form of a vapor, by the process of evaporation. Wick type liquid dispensers, which diffuse an active liquid material into the atmosphere, at a slow controlled rate, are not limited to use as air freshening devices. The active liquid in wick type slow release dispensing devices, may be chosen as a suitable composition for the use as a deodorizer, insecticide, pesticide, insect repellant, animal repellant, animal attractant, and the like. Another use for wick type liquid dispensers is to deliver a liquid pharmaceutical composition from a liquid container, through a wick, to an emanator in contact with the skin, whereby the pharmaceutical composition is slowly delivered and absorbed transdermally into a living body. A further use for wick type liquid dispensers is to deliver liquid nutrients or fungicides to vegetative soil or into the water of hydroponic vegetative cultivations. The examples of wick type dispensing devices mentioned above, all have a common desirable requirement to provide a slow controlled delivery of an active liquid over an extended period of time, through the use of a wick. While wick type liquid dispensing devices are applicable to many different uses with minor modifications, wick type liquid dispensers are especially suited, and commonly used for air freshening devices, thus the prior art is described in particular detail in reference to the use as an air freshener.

Many varieties of wick type dispensers are well known in the art of air freshening devices. Air freshening devices are useful for the purpose of dispensing and diffusing a volatile scent-producing liquid into the atmosphere of homes, public areas, offices, transportation vehicles, and other areas which may exhibit objectionable odors. The scent producing liquid in wick type air fresheners may be available in a variety of different fragrances to treat or mask objectionable odors and provide a long lasting pleasant odor. In order to be effective, the wick type dispensing device must provide the desired fragrance at a slow uniform rate, over an extended period of time. The air freshener would be uneconomical if it would not last long and require frequent replacement. Another problem with prior art wick type air fresheners, is an initial delivery of a large amount of fragrance, and then subsequently a delivery of progressively less fragrance. The initial large dose of fragrance can be objectionable and even cause headaches in certain people, while the subsequent depleted fragrance produces a small dose of fragrance inadequate for the intended objective.

The most basic wick type air freshener is comprised of an absorbent material, impregnated with a scent-producing volatile liquid. The absorbent material acts as the liquid container, wick, and emanator all combined. The scent-producing fragrance is absorbed into the absorbent material by capillary action. The fragrance impregnated absorbent is commonly packaged in a non-permeable wrapper or container to prevent the evaporation of the scent producing liquid into atmosphere, before its intended use. Examples of absorbing material used in prior art are; blotter paper, felt, cellulose, cotton, wood chips, dried vegetation, sponge material, and other porous or fibrous material. The absorbent is commonly shaped or presented in an attractive or decorative manner. The primary disadvantage of the absorbent type of air freshener is its inability to deliver a slow controlled amount of fragrance to the atmosphere. The absorbent type of air fresheners, release a concentrated dose of fragrance quickly when first activated, then over a relatively short period of time the perceived fragrance intensity becomes inadequate in its ability to provide a pleasant fragrance to the atmosphere.

The rate of fragrance evaporation to the atmosphere by the absorbent type of air fresheners, is controlled to a great degree by its exposed surface area and ambient temperature. A large exposed surface area would provide a greater rate of fragrance evaporation. Variations in ambient temperatures also would produce variations in fragrance diffusion rate into the atmosphere. Many of the absorbent type of air fresheners are commonly used inside of transportation vehicles. A disadvantage in the use of this type of air freshener for use in vehicles, is caused by temperature variations commonly encountered in a vehicle. If the vehicle is parked with its windows closed on a hot sunny day, the greenhouse effect of the sun and windows may produce extremely elevated temperature within the vehicle. The elevated temperature will accelerate the evaporation rate of fragrance in an absorbent type of air freshener, to produce an objectionable strong scent in the vehicle. A further disadvantage of the absorbent type of air freshener is the limited volume of the scent-producing liquid, dependent upon the absorption capacity of the absorbent material. Another further disadvantage of the absorbent type of air freshener is the requirement of the relatively large exposed surface area of the absorbent in contact with the atmosphere. A large area of scent-producing liquid in contact with the atmosphere is undesirable, because the absorbent emanator permits a large interface area between the scent-producing liquid and atmospheric oxygen, which can degrade liquid fragrances, thus producing undesirable fragrances.

Many improvements to absorbent type of air fresheners have been devised, to provide increased control over the diffusion of the scent-producing liquid into the atmosphere. One such improvement involves the use of apertures, or more specifically the control of the aperture size of a container, which houses an absorbent, impregnated with a scent-producing liquid. Increasing the effective size of the housing apertures, will increase the rate of scent vapor evaporated into the atmosphere. Conversely, decreasing the effective size of the apertures, will decrease the rate of scent vapor evaporated into the atmosphere. As an example, U.S. Pat. No. 4,549,693 to Barlics et al., discloses a dispenser, comprised of a two part circular housing, containing a round absorbent pad, whereby the effective aperture openings in the housing are controlled by an up and down sliding motion, bringing the apertures in each part, in and out of register. U.S. Pat. No. 4,306,679 to Dusek et al., discloses a dispenser with a two part housing, containing a round absorbent pad, whereby the effective aperture openings in the housing are controlled by a twisting motion, bringing the apertures in each part, in and out of register. A further attempt to control the rate of diffusion in an absorbent type of air freshener, is disclosed in U.S. Pat. No. 4,280,649 to Montealegre. The aperture control in this patent consists of a two part rectangular carton, sliding up and down to provide a means to vary the aperture size. U.S. Pat. No. 4,712,737 to Hecking, discloses another method to control the aperture size in an air freshener housing, by the use of release tape to uncover a plurality of apertures. All of the above patents describe a method to control the rate of diffusion of a scent-producing liquid into the atmosphere, by control of the aperture size in the air freshener container. A basic disadvantage associated with the above patents is the requirement for a user to continually adjust the housing aperture to maintain a desired scent level. A further disadvantage is the limited supply of scent-producing liquid, which is dependent upon the liquid absorbing capabilities of the absorbent.

Improvements to the scent-producing liquid capacity have been made, through the use of two compartment or multicompartment containers, for absorbent type air fresheners. An example of such an improvement is disclosed in U.S. Pat. No. 4,998,671 to Leifheit, whereby the dispenser is comprised of a two compartment flexible bag. The scent-producing fluid compartment is maintained isolated from the absorbent, until time of use. At the time of use, a rupturable barrier is broken, providing a passage from the scent-producing liquid reservoir to the absorbent emanator. The emanator is maintained impregnated with the scent-producing liquid. U.S. Pat. No. 4,762,275 to Herbert et al., discloses a flat rigid container, maintained separated from an absorbent emanator by a puncturable membrane. At the time of use, a pointed element pierces the performable liquid reservoir, providing a passage for the active liquid to maintain the absorbent emanator continuously impregnated. The air freshener dispenser disclosed in U.S. Pat. No. 4,330,079 to Sato et al., discloses a scent-producing liquid reservoir, which is maintained isolated from an absorbent emanator pad until the time of use. At the time of use, a pointed element pierces a rupturable membrane to allow passage of the scent-producing liquid from the reservoir to the absorbent and maintain the absorbent emanator impregnated with the active liquid. A rotary control is also included on the housing, over the emanator pad to control the scent vapor evaporation rate, by varying the register between apertures with a rotary wheel. A disadvantage of the patents disclosed above is their inability to adequately control the amount of scent-producing liquid to the absorbent emanator. The absorbent emanator is maintained saturated with liquid thus producing a high concentration of fragrance vapor. U.S. Pat. No. 4,339,079 also attempts to address this disadvantage through the use of a variable aperture window. Aperture control would be time consuming to a user, requiring constant attention to aperture regulation to maintain a desired fragrance level. A further disadvantage is a result of the relatively large surface area of active liquid, impregnated in the absorbent, in contact with atmosphere oxygen. Degradation by oxygen, of the fragrance over time, may produce undesirable odors.

Numerous modifications to the basic wick in a bottle type of air freshener have also been devised, in an attempt to extend the useful life of a scent dispenser, improve control over the rate of fragrance diffusion, and spill prevention of the scent-producing liquid. In its basic form, a wick in a bottle air freshener consists of a narrow neck bottle container holding the scent-producing liquid, whereby a wick is raised out of the bottle, in contact with the atmosphere at one end, and in contact with the liquid at the other end. Prior to use, the wick is contained within the bottle allowing a cap to seal the bottle and prevent spillage of the scent-producing liquid. An advantage of the bottle container, is in its capacity to hold a relatively large amount of scent-producing liquid, resulting in a prolonged useful life of the dispenser. An example of a wick in the bottle air freshener is disclosed in U.S. Pat. No. 3,091,396 to Curtin. This patent discloses a rigid framework on the wick, to provide a convenient means of varying the scent evaporation rate, by raising and lowering the wick, resulting in a control over the evaporative surface area of the dispenser. Improvements in prevention of potential spillage, of the scent-producing liquid are disclosed in U.S. Pat. Nos.; 4,742,960 to Bustillo et al., 3,724,756 to Maltenfort, 3,207,441 to Schreiber, 3,091,396 to Curtin, and 3,028,100 to Xenakis et al. While the improvements disclosed in the above patents have been found useful, the wick in the bottle type of air freshener does not provide an adequate control, to deliver a scent-producing liquid at a slow constant rate over an extended period of time. Numerous time consuming adjustments and attention must be provided, in an attempt to maintain a desirable fragrance level in the atmosphere. U.S. Pat. No. 4,323,193 to Compton et al., is a further attempt to control the diffusion rate of the scent-producing liquid into the atmosphere at a slow steady rate. The wick is in the form of a sheet, surrounded by a container, with adjustable aperture slots. Constant attention must be provided to adjusting the apertures, to maintain a desirable scent level. A further disadvantage of wick in the bottle dispensers, is the relatively large liquid saturated surface area in contact with the oxygen in the atmosphere. Oxygen can combine with the active liquid, producing undesirable degradation products.

Attempts to provide a slow controlled rate of diffusion by a scent-producing liquid in the atmosphere, have been made by dispensers comprised of; a sealed container holding a scent-producing liquid, a wick to convey the active liquid to an emanator, and an absorbent emanator to provide an evaporative surface area for the liquid diffusion into the atmosphere. U.S. Pat. No. 4,928,881 to Barlics et al., discloses an air freshener with a vented, liquid sealed container for the scent-producing liquid. This patent also describes a wick continuous with an absorbent diffuser pad. The wick is positioned internal to the container and in contact with the scent-producing liquid. The absorbent emanator is positioned on top of the liquid container. A decorative cover provides an aperture in an attempt to control the rate of scent evaporation. Many additional modifications have been devised in an attempt to control the rate of scent diffusion. U.S. Pat. No. 5,014,913 to Hoyt et al., discloses a hinged two part shell cover surrounding the dispenser. An attempt to control the rate of the liquid diffusion is made, by requiring the user to open or close the wings of the shell. U.S. Pat. No. 4,739,928 to O'Neil, discloses an air freshener with a liquid container, wick, emanator pad, and an adjustable aperture cover to control the rate of diffusion. Rotating the cover brings the apertures in and out of register, thereby controlling the diffusion of the scent vapor. U.S. Pat. No. 4,419,326 to Santini, discloses the use of internal rigid porous wicks to regulate the rate of fluid transport to a porous plastic emanator. U.S. Pat. No. 4,915,301 to Munteanu, discloses an improvement over the previously mentioned patent, by the addition of a vent passage. U.S. Pat. No. 4,878,615 to Losi, discloses an air freshener device which requires pumping of an elastic membrane on the liquid reservoir container to replenish an absorbent emanator with scent-producing liquid. The disadvantage of this method is the time consuming attention, required of a user, to maintain a desired scent level. While the inventions disclosed above have been useful in some instances, their use to adequately control the slow constant diffusion of a scent-producing liquid into the atmosphere, are still subject to certain disadvantages. While the use of a sealed rigid liquid container has reduced the problem of liquid spillage, a vent passage from the atmosphere to the head space of the liquid container would be required. If the air freshener dispenser is accidentally knocked on its side, the vent passage could become blocked with the liquid inside the container, or if the vent is large enough, the liquid could slowly leak out of the dispenser. A blocked vent in a sealed dispensing liquid container would result in an increasingly slow dispensing rate and ultimately cease. The above mentioned air freshener devices, generally operate with the absorbent emanators saturated with scent-producing liquid. The relatively large surface area saturated with the scent-producing liquid, provides a large interface area with oxygen from the atmosphere. Atmospheric oxygen may degrade the liquid into compositions producing an undesirable scent. Many air fresheners require the scent-producing liquid to be diluted with another liquid which does not provide a scent. The diluted composition is required for dispensers with relatively large liquid saturated emanators, or an undesirable strong scent would diffuse into the atmosphere. The diluted scent producing liquid requires a relatively large container and precludes the use of a small compact liquid container, containing a concentrated scent-producing liquid. The inventions described above are also limited to placement on only horizontal surfaces, due to the shape of the liquid container. In certain applications, it may be more desirable to mount an air freshener on a vertical wall. A further disadvantage is the control of liquid diffusion, by time consuming attention, required to adjust the apertures on the dispenser.

The use of porous containers and microporous plastic membranes, permeable to the scent vapor but impermeable to the scent-producing liquid, have been used in an attempt to control the rate of diffusion of the liquid into the atmosphere as a vapor, in air fresheners. U.S. Pat. Nos. 4,948,047 to Zembrodt, and 4,634,614 to Holzner describes the use of a microporous plastic membrane to control the diffusion rate of a scent-producing liquid into the atmosphere. A further modification is described in U.S. Pat. No. 4,753,389 to Davis. The scent-producing liquid is stored in an absorbent material, inside a sealed container with a vapor plenum cavity which is sealed by a vapor permeable cap. The cap orifice area and the vapor permeable barrier, control the diffusion rate of the scent-producing liquid. U.S. Pat. No. 4,614,299 to Loveren et al., describes a dispenser comprised of a flexible microporous plastic inner pouch surrounded by a vapor impermeable outer pouch for storage. The inner pouch also contains a scent-producing liquid in the form of a gel. The diffusion of scent-producing gel is controlled by the vapor permeable properties of the plastic pouch. Porous ceramic containers have also been used to contain the scent-producing liquid, while allowing the scent vapors to diffuse through the container wall. A disadvantage common to air fresheners using a vapor permeable membrane or vapor permeable container to control the rate of scent diffusion, is their susceptibility to pore blockage and scent composition fractionating. The pores of the microporous container can become blocked if the air freshener is knocked on its side allowing the scent-producing liquid to coat the vapor permeable pores of the material. The scent-producing liquid may also be subjected to composition fractionating by vapor diffusion through the micropores. The most volatile vapors will pass through the micropores first, and subsequently the least volatile vapors of the fragrance composition will be diffused into the atmosphere last, resulting in a distortion of the scent over time.

The point made by these examples of prior art is, that while these liquid dispensing devices are somewhat satisfactory in some circumstances, the prior art devices are limited by the aforementioned disadvantages, thus there remains a need for an improved liquid dispensing device, capable of slow controlled dispensing and diffusion of liquids and vaporizable materials.

OBJECTS OF THE INVENTION

It is a primary object of the present invention to provide an improved liquid dispensing devive for the slow controlled dispensing and diffusion of liquids and vaporizable material over an extended period of time.

More specifically, an object of the present invention is to provide a liquid dispensing device for use as, but not limited to: diffusing volatile liquids into the atmosphere such as in the use of air fresheners, a pharmaceutical delivery device such as in the use for transdermal infusions, a nutrient delivery device for vegetative cultivations grown in soil or water, and other applications where a slow controlled dispensing of an active liquid is desired.

A further object of the present invention is to control the slow uniform rate of liquid dispensing, by means of a selected length and diameter of a narrow absorbent wick, covered by an impermeable tube with open ends, whereby the covered wick prevents lateral evaporation and plugging absorbent pores by the less volatile components of the active liquid.

Another object of the present invention is to provide a flexible storage pouch or bag to contain an amount of active liquid used over an extended period of time, whereby as the liquid is dispensed, the plastic pouch collapses with the reduced internal volume, obviating the requirement for a vent in the liquid container.

Another object of the present invention is to provide a liquid dispenser with a flexible external tubular wick, allowing the diffusing emanator location remote from the active liquid reservoir, thereby resulting in a great deal of freedom in mounting locations for the device.

A further object of the present invention is to provide a liquid dispensing device for the slow controlled delivery of active liquid to the diffusing emanator, whereby the emanator diffuses only small amounts of active liquid, as the dispensing rate is controlled by the narrow wick inside a tubular element, thus preventing the emanator from operating saturated with the active liquid, and minimizing the distortion of fragrance caused by fractionating and atmospheric oxygen degradation.

Still another object of the present invention is a means to maintain the wick isolated from the active liquid prior to use, by a removable or rupturable barrier.

Another object of the present invention is to provide a liquid dispensing device which is contained in a sealed non-spillable package.

The present invention which satisfies one or more of the above objects of the invention, is presented in the summary of the invention which follows.

SUMMARY OF THE INVENTION

The present invention is an improved wick type liquid dispensing device, useful for dispensing and diffusing liquids and vaporizable material at a slow controlled rate, over an extended period of time. The present invention is particularly suitable for applications requiring a slow uniform dispensing of an active liquid. With only minor modifications, the present invention may be used in a number of applications. The following examples are not intended to limit the invention in any manner. In addition to other uses, the present invention may be used to dispense and diffuse volatile liquids into the atmosphere, for example as in air fresheners. The present invention may also be used to dispense pharmaceutical material through the process of transdermal infusion by a skin patch emanator. Another use for the present invention is to deliver nutrients and fertilizer compositions to the soil of vegetative cultivations or to the water of hydroponic vegetation.

The primary advantages of the present invention is the slow controlled dispensing of an active liquid material to a required location by a use of a wick enclosed within an impermeable tube, open at each end. The absorbent wick conveys the active liquid by capillary action, from a liquid reservoir to another location for diffusion. The active liquid is stored in a sealed flexible plastic pouch or bag, which eliminates the need for venting and prevents liquid spillage.

In its simplest form, the present invention may be said to consist of a sealed flexible pouch or bag acting as a reservoir containing the active liquid, and a wick enclosed by a impermeable tubular element which is open at each end, to convey the active liquid from the liquid reservoir to diffusing emanator. The emanator may be an absorbent material to provide a diffusing surface area, or the emanator may just be the end of the wick. One end of the tubular covered wick protrudes into the flexible pouch or bag, whereby the tubular wick cover maintains a liquid seal to the pouch or bag, at the same time allowing the inner absorbent wick to contact the active liquid and convey the liquid by capillary action, to the other side of the wick in contact with the diffusing emanator. The wick inside the pouch or bag is maintained isolated from the active liquid prior to use. The active liquid may be maintained isolated from the wick prior to use, by enclosing the liquid in a frangible container within the bag or pouch, or by the use of rupturable or removable barrier strips. The dispenser could be contained in an attractive housing for aesthetic purposes or the reservoir container could be maintained remote from the emanator for functional purposes.

The rate of active liquid dispensing from the reservoir container to emanating surface is primarily controlled by the dimensions of the wick. The wick must be absorbent enough to maintain capillary action along its entire length. A smaller diameter long wick, will result in a slower liquid dispensing rate, when compared to a larger diameter shorter wick. An impermeable tube surrounding the wick prevents active liquid loss caused by lateral evaporation along the wick's length. The relatively slow travel of the active liquid, results in extended liquid dispensing times and allows the use of compact reservoirs of concentrated active liquids.

The liquid dispenser operation is initiated by removing or rupturing the barrier between the active liquid and the wick. The wick quickly becomes saturated with the active liquid within the reservoir pouch or bag. The active liquid is conveyed along the length of the shielded wick to the other end, in contact with the diffusion emanator. As the active liquid is diffused by the emanator at a slow rate, more liquid is supplied to the emanator at a slow controlled rate, through the shielded wick.

DESCRIPTION OF DRAWINGS

Other objects, advantages, and features of the present invention will become more apparent from the drawings and the detailed description of the invention relating to the drawings, in which a preferred embodiment of the invention is illustrated wherein like parts are identified by like reference characters in each of the figures and in which: all of the figures are in accordance with the invention, and in which the figures depict the invention's liquid reservoir container, as constructed of a transparent polymeric material as examples, for a better understanding of the invention. It will be understood, the liquid reservoir container material is not limited to consisting of transparent polymeric material.

DETAILED DESCRIPTION OF THE INVENTION

What follows is a detailed description of the present invention and particularly a description of the preferred embodiments which constitute the best mode of carrying out the present invention. This description exemplifies the present invention but is not intended to limit the scope of the invention. It will be understood that no limitations of the scope of the present invention is intended by the examples of the illustrated dispenser, and by further applications and uses of the principles of the invention which would normally occur to one skilled in the art. It will be further understood that the invention is not limited in its application to the details of construction and arrangement of parts illustrated in the accompanying drawings, since the invention is capable of other embodiments and being practiced or carried out in various ways. Also, it will be understood that the phraseology and terminology employed herein is for the purpose of description and not a limitation.

While the present invention is applicable to a slow controlled liquid dispenser adapted for many different applications and uses, it is especially suitable for use as an air freshener dispenser, transdermal pharmaceutical dispenser, and a vegetative cultivation nutrient dispenser. Thus, the present invention will be described with particular reference to these three specific uses. In order to more completely describe the present invention, it is necessary to define several of the terms used herein as follows:

The flexible liquid container will be referred to as a bag, a pouch, or the liquid reservoir. The barrier or barrier strip, refers to a means to keep the active liquid in the reservoir isolated from the wick, prior to use. The emanator con simply be the end of the wick assembly, or a material at the end of the wick assembly to distribute the active liquid over a given surface area. The emanator is located on the end of the wick assembly, opposite from the reservoir bag. The active liquid, refers to the liquid material inside the reservoir bag, and is dependent upon the intended use of the liquid dispenser. Some examples of active liquids are: fragrance compositions, pharmaceuticals, and vegetative nutrients.

Figure 1:
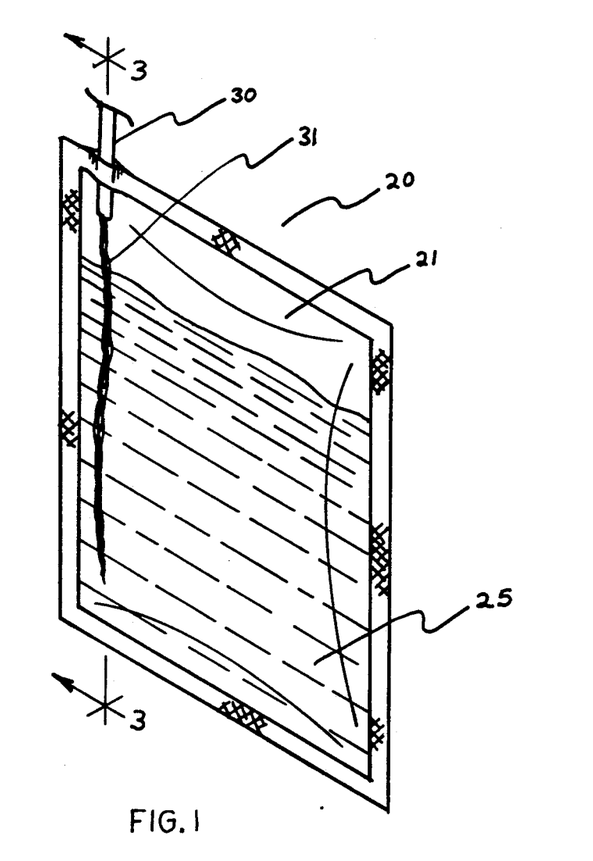
FIG. 1 Is a perspective view of the liquid dispenser reservoir container and wick assembly, in contact with the active liquid and illustrated in the activated mode after removing or rupturing the liquid to wick isolation barrier. For reasons of clarity, the external wick assembly is not shown in its entire length terminating in a diffusing emanator.
Figure 2:
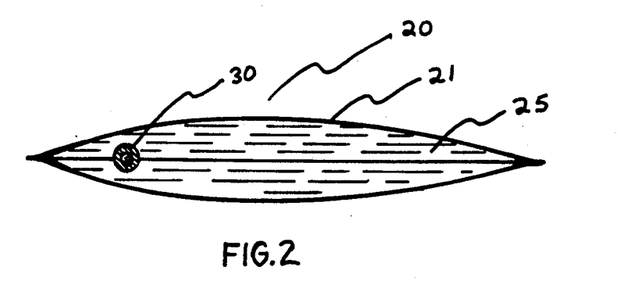
FIG. 2 Is a top view of FIG. 1, further illustrating the general shape of the liquid reservoir container and wick location.
Figure 6:
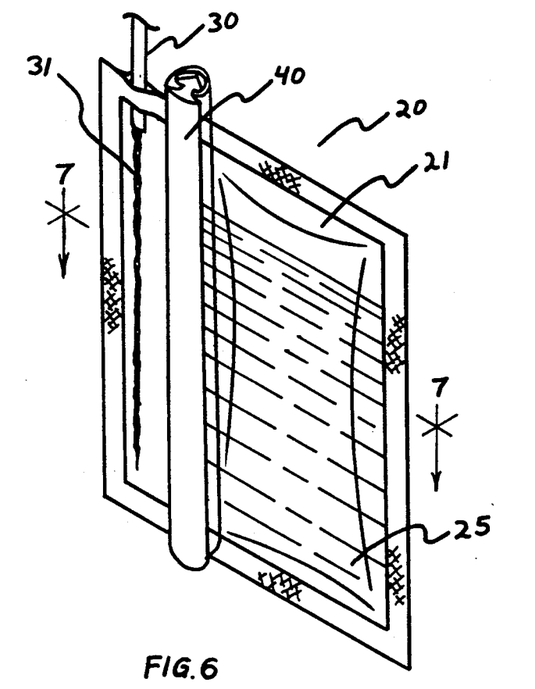
FIG. 6 Is a perspective view of the liquid reservoir and wick assembly prior to use, illustrating a removable barrier strip along the reservoir container, pinching the two sides of the container together, resulting in a liquid barrier, effectively isolating the active liquid from the wick prior to use.

In its simplest form, the present invention may be said to consist of a sealed flexible bag, containing an active liquid, with a wick assembly conveying the active liquid to an emanator at a slow controlled rate, also including a barrier means to maintain the active liquid isolated from the wick prior to use. Referring now to FIGS. 1 and 6, a preferred embodiment of the flexible bag reservoir assembly 20 is shown comprising of a flexible polymeric bag 21 generally planar in shape sealed along its periphery, including a protrusion by the wick assembly 30 through the bag, allowing active liquid 25 contact with the wick 31 after the barrier strip 40 is removed.

Figure 3:
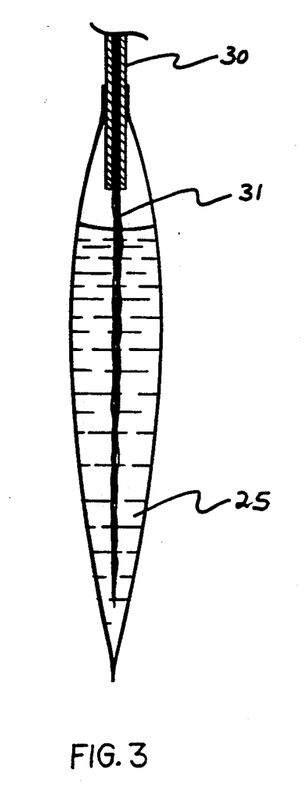
FIG. 3 Is a side sectional view of the sealed wick assembly in the reservoir container, taken along line 3—3 of FIG. 1, illustrating the general location of the wick assembly in the reservoir container.

The dispenser reservoir 20 is constructed of a flexible polymeric material 21 which is capable of collapsing inward in response to the reduced volume, as the active liquid 25 is depleted. The polymeric reservoir bag material 21 must also be impermeable and compatible with the active liquid 25. The shape of the generally planar bag 21 is not limited to a rectilinear shape as depicted in the drawings. The flexible polymeric bag material may be constructed of, but not limited to polyethylene, polyvinyl chloride, polypropylene, polyacrylates, polyamides, polycarbonates, polyvinylidene chloride, ethyene vinyl acetate, polystyrene, polyfluorocarbons, polyesters, metallized polymeric films, composite polymeric laminates, and composite polymeric coextrusions. The flexible bag reservoir 20 may be constructed by welding the periphery of two polymeric sheets by means of heat, adhesives, or ultrasonic energy. Alternatively, the flexible bag 20 may be constructed by folding one edge and welding the remaining edges or beginning with a thin tubular polymeric material and welding the top and bottom of the bag. Flexible bag form, fill, and sealing machines which may be used are commercially available. The wick assembly 30 protrudes through the reservoir 20. The outside of the wick assembly must maintain a liquid-tight with the bag 20. This seal may be accomplished by thermal welding or through the use of polymeric fitments welded onto the bag 20. FIG. 3 illustrates a thermal weld seal between the polymeric bag material 21 and the wick assembly 30.

Figure 7A:
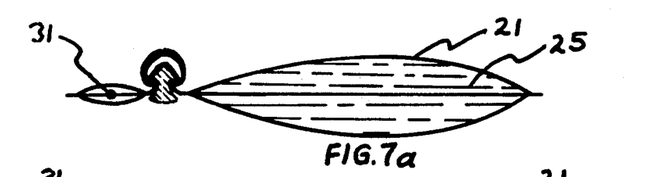
FIGS. 7a, 7b, and 7c, are sectional views of the liquid reservoir container and the removable barrier strip, taken along the line 7—7 of FIG. 6, illustrating examples of various embodiments of barrier strips pinching the container sides together effectively maintaining the active liquid isolated from the wick prior use.
Figure 7B:
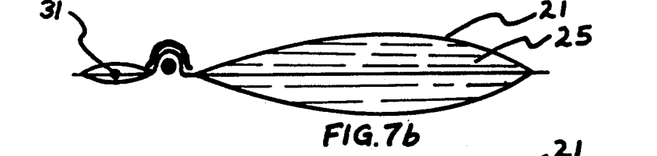
Figure 7C:
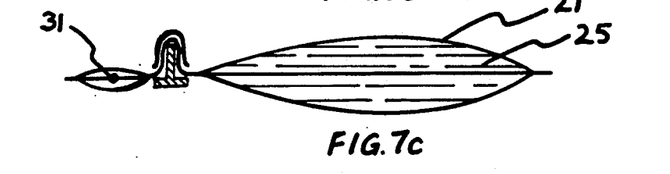

A preferred embodiment of the invention is shown in FIG. 6 wherein a barrier strip 40 isolates the active liquid 25 from the wick 31 located in the wick assembly 30, prior to use. The barrier strip 40 maintains a clamping pressure, pinching the sides of the polymeric bag 20 together effectively isolating the active liquid 25 from the wick 31. The barrier strips 40 are separated when the liquid dispenser is ready for use. After removing the barrier, the active liquid 25 is free to contact the wick 25, and begin its travel by capillary action to the emanator. FIGS. 7a, 7b, and 7c illustrate sectional view examples of interlocking barrier strips. It will be understood the barrier strips of this invention are not limited to the examples illustrated. Any means of maintaining the active liquid isolated from the wick would serve the purpose of the barrier strip 40.

Figures 8, 9:
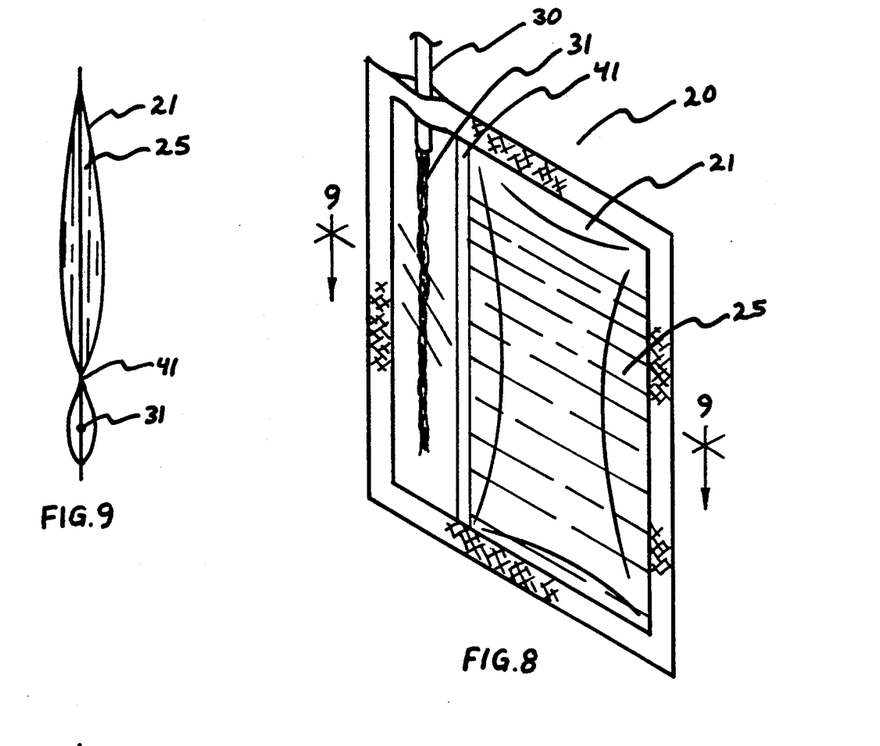
FIG. 8 Is a perspective view of the liquid dispenser reservoir container and wick assembly prior to use, illustrating another means of maintaining the active liquid isolated from the wick by the use of a rupturable barrier strip.
FIG. 9 Is a sectional view of the liquid reservoir container and the rupturable barrier strip, taken along line 9—9 of FIG. 8, illustrating the barrier strip maintaining the active liquid isolated from the wick prior to use.

Another embodiment shown in FIG. 8 is similar to the embodiment shown in FIG. 6. However, this embodiment has a rupturable seal barrier strip. The rupturable seal is located in between the walls of the reservoir bag 20. The seal 41 forms a liquid compartment to isolate the active liquid from the wick prior to use. The rupturable barrier seal 41 could be made of a polymeric foam or a weak heat weld whereby, the application of external pressure by squeezing the bag walls together would rupture the seal 41 and allow the active liquid 25 to contact the wick 31.

Figures 10, 11:
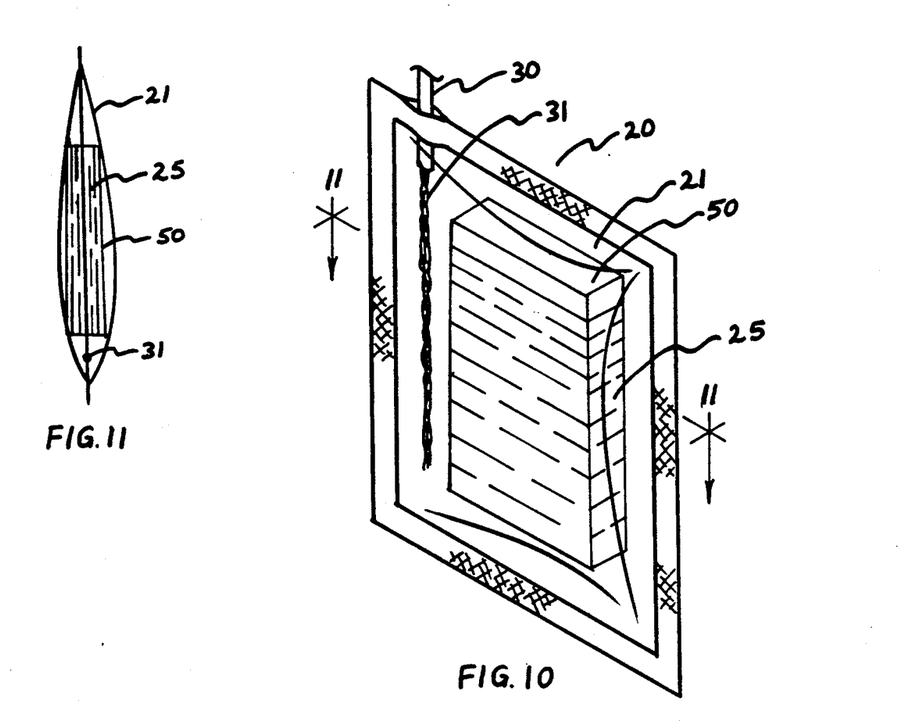
FIG. 10 Is a perspective view of the liquid dispenser reservoir container, wick assembly, an example of an internal frangible container, containing the active liquid and maintaining the active liquid isolated from the wick prior to use.
FIG. 11 Is a sectional view of the liquid reservoir container, wick assembly, and internal frangible container, taken along line 11—11 of FIG. 10, illustrating an example of the location of the frangible container.

A further embodiment shown in FIG. 10 is similar to the embodiment shown in FIG. 6. However, this embodiment maintains the active liquid in a frangible container 50 within the reservoir bag. External pressure applied by squeezing the sides of the reservoir bag together, will rupture the frangible container 50, and allow the active liquid 25 to contact the wick 31.

A variety of other methods to keep the active liquid isolated from the wick prior to use can be used as a barrier for this invention. For example, a complementary rib and groove strip could be welded to the interior walls of the reservoir bag. The liquid interlocking profile would keep the active liquid isolated from the wick prior to use. At the time of use, the reservoir bag walls could be pulled apart, opening the barrier strip, and allowing the active liquid to contact the wick. Any type of rupturable or removable liquid barrier could be used in this invention, to maintain the active liquid isolated from the wick, prior to use.

The wick assembly 30 extends in a continuous manner from the emanator, through the reservoir bag, and in contact with the active liquid within the reservoir bag. A feature of the present invention is that the wick is external to the liquid container allowing the emanator to be located remote from the liquid container. This feature allows freedom in location placement of the liquid container and the liquid emanator. The flow rate of active liquid volume over time, can be regulated by the dimensions of the wick. A narrow long wick will convey less active liquid to an emanator than a short thick wick. The wick will deliver an active liquid slowly over an extended period of time, to prevent liquid saturation of the emanator. As the active liquid is depleted within the reservoir bag, the bag collapses inward, in response to the reduced volume, obviating the need for an atmospheric vent. The wick 31 acts as a conduit to continuously replenish the supply of active liquid to the emanator, as the remaining liquid on the emanator is diffused. A plurality of wicks may be utilized to convey an active liquid from a common reservoir to individual emanators at remote locations.

Figure 4:
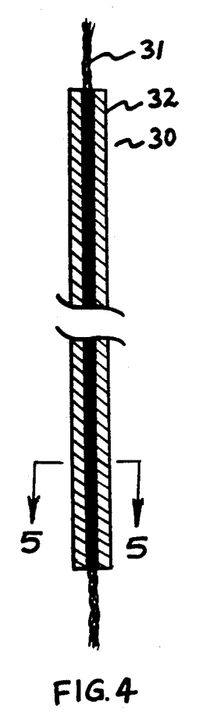
FIG. 4 Is a sectional view, of a partial length of the wick assembly, taken along its length, illustrating the location of the absorbent wick relative to the impermeable tubular covering.
Figure 5:
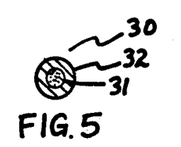
FIG. 5 Is a sectional view of the wick assembly, taken along line 5—5 of FIG. 4, illustrating the relative location of the absorbent wick to the impermeable tubular covering.
Figure 14:
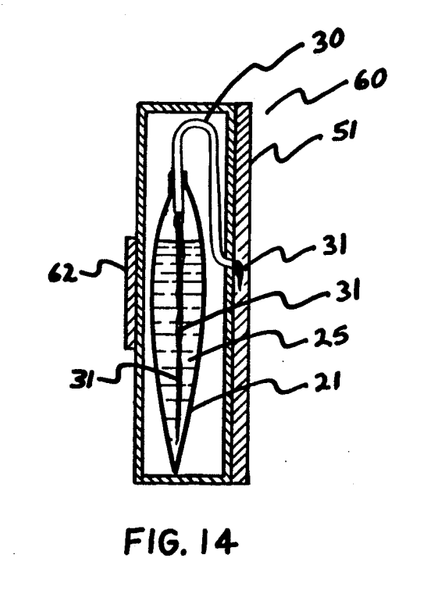
FIG. 14 Is a sectional view of the invention used as an air freshener device, taken along line 14—14 of FIG. 12, illustrating the location of the dispensing device within the aesthetic housing.
Figure 15:
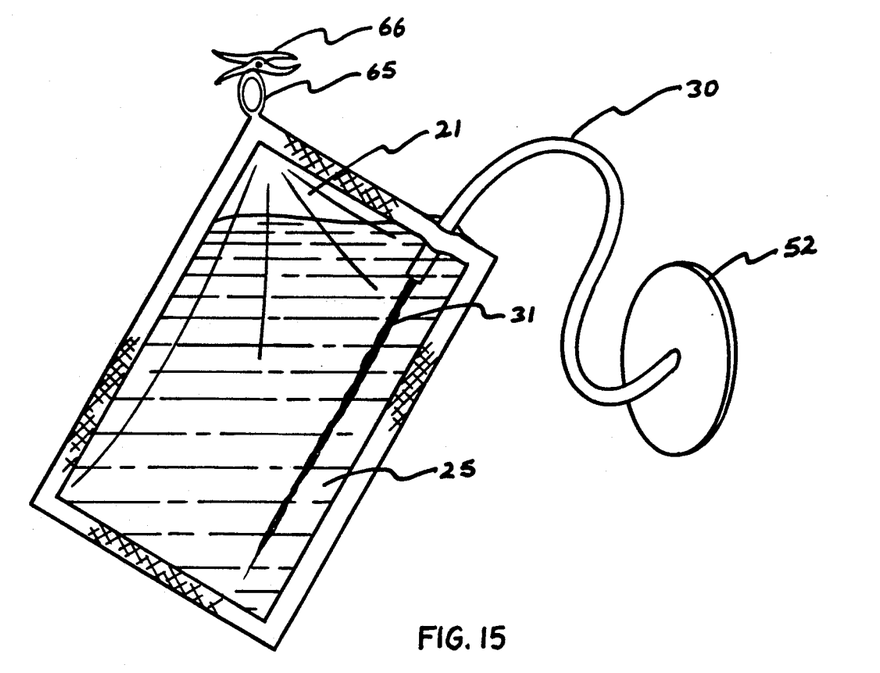
FIG. 15 Is a perspective view of another preferred embodiment of the invention used as a transdermal infusion device to dispense a pharmaceutical active liquid.
Figure 16:
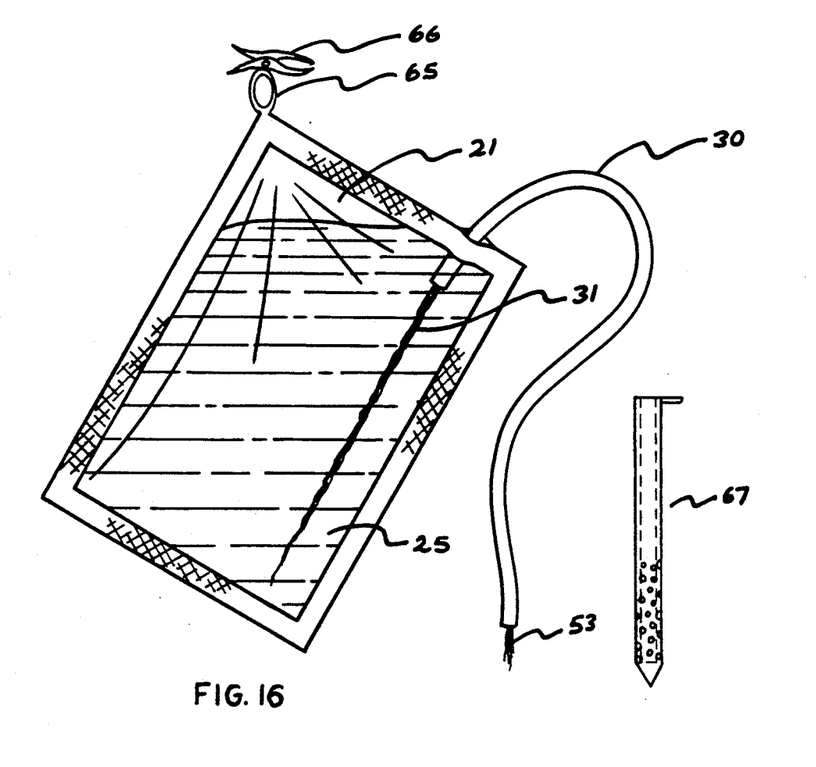
FIG. 16 Is a perspective view of another preferred embodiment of the invention used as a liquid nutrient dispenser for vegetative cultivations.

Details of the wick 31 an the wick assembly 30 are shown in FIGS. 4 and 5. The wick 31 is located within a hollow impermeable tubular element 32. The wick 31 is made of absorbent material capable of conveying a liquid by capillary action. Some examples of wick material are: cotton, cellulose fiber, synthetic polymeric fibers or foams, felt, and porous ceramics. The wick in present invention can be made of any material capable of conveying a liquid by capillary action. The wick assembly 30 is comprised of the aforementioned wick 31, surrounded by an impermeable tubular element 32. The impermeable tubular element 32 enclosing the wick, shields the active liquid being conveyed and prevents lateral evaporation of the liquid along the wick surface. The tubular element 32 could be comprised of polymeric or metallic material depending on the desired properties, such as flexibility for an example, and also compatibility with the active liquid. The embodiment of the invention shown in FIG. 14 uses polyethylene material for the tubular element 32, and cotton material for the wick 31, in the wick assembly 30. However, the present invention is not limited to the materials given as an example. Additionally, the present invention includes shape modifications of the sectional shape of the wick assembly 30. For example, in FIG. 5 the tubular element 32 could be rectangular, triangular, or flat. The tubular element 32 of the wick assembly 30 is open on each end, allowing a portion of the wick 31 to extend beyond the tubular element 32 at each end. As shown in FIGS. 1, 3, 6, 8, 10, 14, 15, and 16, the wick 31 extends well beyond the wick assembly into the reservoir bag to ensure good contact with the active liquid during the dispensing period. The other end of the wick 31 is affixed to the dispersing emanator as shown in FIGS. 14, 15, and 16. The tubular element 32 of the wick assembly 30 can also provide a secure mechanical bond to the emanator. The wick 31 extends beyond the tubular element 32 making physical contact with the emanator 51, 52, and 53 thus, conveying the active liquid to the emanator. The emanator may be orificed to receive the wick.

The emanator is the diffusing element of the liquid dispenser. The design of the emanator will be dependent upon its intended use. For example, the end of the wick 31 alone may serve the purpose of an emanator when one embodiment of the invention as shown in FIG. 16 is used to deliver a liquid nutrient to the soil or water of vegetative cultivation. The water or soil will act upon the end of the wick 31 to disperse the active liquid. In another embodiment shown in FIGS. 12, 13, and 14, the invention could be used as an air freshener to convey a volatile liquid fragrance composition to an absorbent emanator 51. The emanator in this case would serve to disperse the volatile liquid into the atmosphere, by the process of evaporation. The emanator 51 is comprised of any absorbent material capable of conveying the active liquid over a relatively large surface area to aid in its evaporation process. Some examples of suitable absorbent emanator material are: felt, blotter paper, porous sponge, cellulose fibers, porous ceramics, and porous polymers. Additionally, the emanator may be fabricated in an aesthetically pleasing or functional shape. For example, the emanator could be fabricated in the shape of a flower, wherein the wick assembly acts as the flower stem, and the reservoir bag could be contained in a vase or pot. In a further embodiment as an air freshener, the emanator of the invention may be formed into a shape characteristic of the scent. For example, the emanator may be shaped as a strawberry, apple, or cherry whereby, the diffused scent would be characteristic of a strawberry, apple, or cherry. In a further embodiment the invention may be used to dispense a pharmaceutical composition transdermally as shown in FIG. 15. The emanator 52 in this application, may be constructed if any absorbent material capable of diffusing the active liquid from the end of the wick 31, over a specified surface area in contact with the skin. Further, the emanator 52 may include an impermeable covering on the outer side opposite the skin side, for protection and also to prevent the loss of the pharmaceutical through evaporation. Further, the emanator 52 may also include an adhesive, to bond the emanator to the skin.

The active liquid 25 in the aforementioned embodiments is dependent upon the use of the present invention. FIG. 14 shows an embodiment whereby the present invention is used as an air freshener. The active liquid 25 may be any scent producing liquid composition or mixture capable of producing a desired odor. FIG. 15 shows an embodiment of the present invention used to deliver a pharmaceutical composition transdermally. The active liquid in this case could be any pharmaceutical composition in liquid form which can be effectively delivered by transdermal means. Some examples of pharmaceutical compositions which can be administered transdermally are nitroglycerine and nicotine. FIG. 16 shows an embodiment of the present invention used to deliver nutrients to vegetative cultivations grown in soil or grown hydroponically. The active liquid in this case can be any vegetative nutrient in liquid form.

The following examples are given as particular embodiments of the invention to demonstrate the practice and advantages thereof. It will be understood that the examples are given by way of illustration and are not intended to limit the specification or the claims to follow in any manner.

Figure 12:
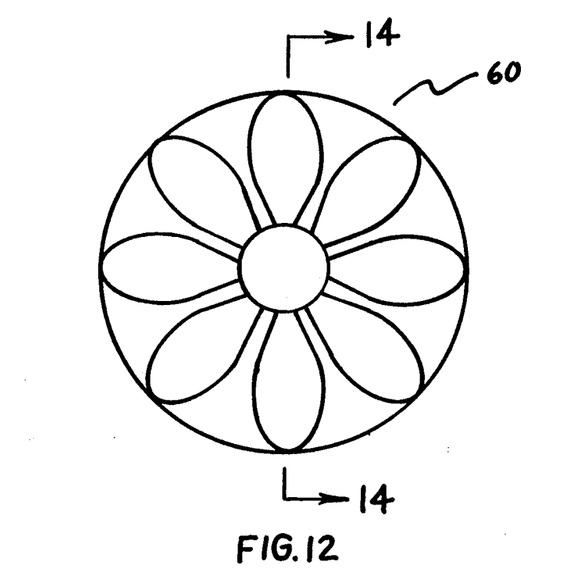
FIG. 12 Is an elevation view of one preferred embodiment of the invention used as an air freshener, whereby the liquid dispenser is housed in aesthetically pleasing container, with the discharge end of the wick protruding through the housing in contact with an absorbent diffusing emanator mounted on the housing.
Figure 13:
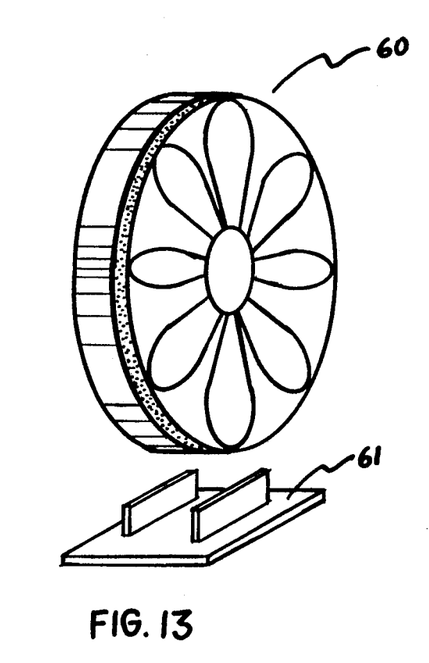
FIG. 13 Is a perspective view of the air freshener illustrated in FIG. 12, depicting an example of one possible housing configuration, when the present invention is used as an air freshener device, also including an optional horizontal surface mounting adapter.

FIGS. 12, 13, and 14 show an embodiment of the present invention used as an air freshener. The reservoir bag 20 and wick assembly 30 is enclosed in a decorative rigid housing 60, chosen to be aesthetically appealing and functional. Although the air freshener example is depicted as a round shape embodiment, the air freshener housing shape may actually be any shape capable of containing the reservoir bag 20 and wick assembly 30. The wick assembly 30 protrudes through the housing to allow physical contact between the wick 31 and emanator 51. The wick 31 inside the wick assembly 30, conveys the scent producing liquid to the emanator. A feature of this embodiment is the compact size of the air freshener, and the air freshener can easily be adapted to vertical mounting through the use of fasteners, hook and loop tape, or pressure sensitive adhesives 62. The air freshener may also be adapted to horizontal mounting through the use of a planar base or an optional planar base support 61. The emanator may be manufactured into an aesthetically pleasing shape and decorated with indicia.

FIG. 15 shows an embodiment of the present invention used as a liquid transdermal pharmaceutical dispenser. The reservoir bag 20 may be conveniently mounted by a hook 65 or a clamping clip 66, remote from the emanator. The location of the hook 65 or clip 66 can be anywhere on the bag. The wick 31 inside the wick assembly 30, conveys the pharmaceutical composition to the emanator 52 in contact with the skin. The emanator 50 may be covered with an impermeable back covering to protect the emanator and prevent the pharmaceutical composition from evaporating into the atmosphere. A pressure sensitive adhesive on portions of the emanator patch may be used to fasten the emanator onto the skin, to ensure effective transdermal dispensing of the pharmaceutical.

The embodiment shown in FIG. 16 shows the present invention used to deliver nutrients in the form of a liquid to vegetative cultivations. The reservoir bag 20 can be conveniently mounted by a hook 65 or a clip 66, remote from the emanator. The hook or clip may be located anywhere on the bag. The wick 31 inside the wick assembly 30, conveys the vegetative nutrient to the emanator. The emanator 53 in this embodiment, of the invention consists of the wick at the end of the wick assembly 30. The soil in which the vegetative cultivation is grown, acts upon the emanator 53 to disperse the liquid nutrient throughout the soil. An optional hollow perforated spike 67 can be used to facilitate the placement of the emanator 53 underground. The emanator 53 is placed within the perforated hollow spike, then the spike is pushed into the soil with the aid of a lip on its top. The embodiment of the invention shown in FIG. 16 could also be used to supply nutrients into the water of hydroponically grown vegetative cultivations, by immersing the emanator 53 into the hydroponic water.

The operation of the liquid dispenser is initiated by the removal of the barrier separating the wick 31 from the active liquid 25. The barrier may be in the form of an element which divides the flexible bag into two compartments, one compartment containing the active liquid 25, and the other compartment containing the wick 31. The barrier may also be in the form of the active liquid contained in a frangible container 50 within the flexible reservoir bag 20 to maintain the Active liquid 25 isolated from the wick 31 prior to use. Upon removal of the barrier, the active liquid will contact the wick 31 and travel by capillary action along the wick onto the emanator. The wick will sustain a flow of a sufficient quantity of active liquid to continuously replenish the emanator over an extended period of time, as the emanator diffuses the active liquid to a desired material. The sealed flexible reservoir bag collapses inward in response to the reduced liquid volume during the dispensing period, providing a liquid container with reduced volume, thus obviating problems of spillage and the need for a vent to the atmosphere.

Although this invention has been described by references to the illustrated embodiments, it will be understood the present invention disclosure has been by way of example and numerous modifications in the details of construction, arrangement of parts, and shapes of parts by a person skilled in the art, are to be included within the scope of this invention as defined in the appended claims.

What is claimed is:

1. A liquid dispensing device containing a supply of scent-producing liquid stored in a liquid reservoir, which maintains said scent-producing liquid supply in isolation from the ambient atmosphere, whereby during functional operation, an absorbent wick, forming part of a wick assembly makes contact with said scent-producing liquid whereby said wick conveys by capillary action said scent-producing liquid at a slow substantially constant rate to the opposite end of said wick which is in physical contact with an evaporative surface of an emanator remote from said liquid reservoir, wherein said emanator diffuses said scent-producing liquid into the ambient atmosphere by the process of evaporation wherein:
  A. said liquid reservoir comprises a generally planar bag formed by the peripheral union of two wall members, said wall members being comprised of impermeable flexible polymeric film material and being sealed together in a continuous manner along their edgewise periphery providing a liquid-tight peripheral seal, wherein a passageway extends through said peripheral seal to accommodate the protrusion of said wick assembly between said wall members, wherein a liquid-tight seal is additionally maintained between said periphery seal and said wick assembly;
  B. said wick assembly extending in a continuous manner from said evaporative surface of said emanator protruding through said liquid reservoir container and making physical contact with said scent-producing liquid during functional operation, and wherein said wick assembly comprises said absorbent wick laterally enclosed within a hollow impermeable tubular element, wherein said tubular element is open at each end allowing a portion of said wick to extend beyond said tubular element at each end, and wherein said wick makes physical contact with said evaporative surface of said emanator at one end and during functional operation said wick on the other end makes physical contact with said scent-producing liquid in said liquid reservoir;
  C. said emanator comprising an absorbent material capable of absorbing said scent-producing liquid into the ambient atmosphere by the process of evaporation;
  D. said scent-producing liquid being maintained isolated from said wick prior to functional operation by means of a containment member, whereby upon removal of said containment member said scent-producing liquid is free to contact said wick thus, commencing the functional operation of said liquid dispensing device.

2. The dispenser of claim 1, wherein said liquid reservoir comprises said impermeable flexible polymeric film material selected from the group comprised of polyethylenes, polypropylenes, polyvinyl chlorides, polyacrylates, polyamides, polyesters, polycarbonates, polyvinylidene chlorides, ethylene vinyl acetates, polystyrenes, modified polystyrenes, polyflurorocarbons, metallized polymeric films, composite laminates or coextrusions of aforementioned films.

3. The dispenser of claim 2, wherein said wick comprises absorbent material selected from the group comprised of woven cotton fibers, nonwoven cotton fibers, woven synthetic fibers, nonwoven synthetic fibers, porous polymeric foams, and porous ceramics, wherein said absorbent wick material is capable of conveying said scent-producing liquid by capillary action and wherein said tubular element comprises impermeable material selected from the group comprised of metals and polymers.

4. The dispenser of claim 3, wherein said scent-producing liquid is maintained in a compartment isolated from said wick prior to removal of said containment member, said containment member comprising removable male-female interlocking barrier strips dividing said liquid reservoir into two liquid-tight compartments, wherein said barrier strips exert a clamping pressure applied on each side of said liquid reservoir wall members interposed between said barrier strips, wherein said wall members are pinched together effectively isolating said scent-producing liquid from said wick prior to functional operation, and wherein removal of said barrier strips permit said scent-producing liquid to contact said wick to commence the functional operation of said dispenser.

5. The dispenser of claim 3, wherein said scent-producing liquid is maintained in a compartment isolated from said wick prior to removal of said containment member, said containment member comprising a rupturable barrier seal interposed between said liquid reservoir wall members, wherein said rupturable barrier seal effectively divides said liquid reservoir into two liquid-tight compartments, and wherein rupture of said barrier seal by external pressure applied against said liquid reservoir wall members permit said scent-producing liquid to contact said wick to commence the functional operation of said dispenser.

6. The dispenser of claim 3, wherein said scent-producing liquid is maintained in a compartment isolated from said wick prior to removal of said containment member, said containment member comprising a frangible container wherein said frangible container contains said scent-producing liquid and whereby rupture of said frangible container by external pressure applied against said reservoir wall members permit said scent-producing liquid to contact said wick to commence the functional operation of said dispenser.

7. The dispenser of claim 3, enclosed in a rigid housing, said housing being orificed to allow said wick assembly to protrude through said housing, and wherein said emanator is located external to said housing to permit the scent-producing liquid to diffuse into the atmosphere.

8. A liquid dispensing device containing a supply of a pharmaceutical liquid stored in a liquid reservoir which maintains said pharmaceutical liquid supply in isolation from the ambient atmosphere, whereby during functional operation, an absorbent wick forming part of a wick assembly, having a foot end, makes contact with said pharmaceutical liquid, whereby said wick conveys by capillary action said pharmaceutical liquid at a slow substantially constant rate to the opposite end of said wick which is in physical contact with a diffusing surface of an emanator remote from said liquid reservoir, wherein said emanator diffuses said pharmaceutical liquid onto the skin of a living organism, whereby the pharmaceutical liquid is absorbed transdermally into the living organism wherein:
  A. said liquid reservoir comprises a generally planar bag formed by the peripheral union of two wall members, said wall members being comprised of, impermeable flexible polymeric film material, and being sealed together in a continuous manner along their edgewise periphery providing a liquid-tight peripheral seal, wherein a passageway extends through said peripheral seal to accommodate the protrusion of said wick assembly between said wall members wherein a liquid-tight seal is additionally maintained between said periphery seal and said wick assembly;
  B. said wick assembly extending in a continuous manner from said liquid reservoir to the emanator and making physical contact with said pharmaceutical liquid supply during functional operation, and wherein said wick assembly comprises said absorbent wick laterally enclosed within a hollow impermeable tubular element, wherein said tubular element is open at each end allowing a portion of said wick to extend beyond said tubular element at each end, and wherein said wick makes physical contact with said diffusing surface of said emanator at one end, and during functional operation said wick on the other end makes physical contact with said pharmaceutical liquid supply in said reservoir;

C. said emanator comprising an absorbent material capable if absorbing said pharmaceutical liquid and diffusing said pharmaceutical liquid into the skin of the living organism, and wherein said emanator is covered by a flexible impermeable film on the side opposite the skin, wherein the impermeable film is orificed to permit said wick to protrude through said impermeable film to said absorbent diffusing surface of said emanator and permit physical contact between said wick and said emanator absorbent material, and wherein said emanator surface is coated with a pressure sensitive adhesive on selected portions of the emanator surface in contact with the skin;

D. said pharmaceutical liquid being maintained isolated from said wick prior to functional operation by means of a containment member, whereby upon removal of said containment member said pharmaceutical liquid is free to contact said wick, thus commencing the functional operation of said dispensing device.

9. The dispenser of claim 8, wherein said liquid reservoir comprises said impermeable flexible polymeric film material selected from the group comprised of polyethylenes, polypropylenes, polyvinyl chlorides, polyacrylates, polyamides, polyesters, polycarbonates, polyvinylidene chlorides, ethylene vinyl acetates, polystyrenes, modified polystyrenes, polyfluorocarbons, metallized polymeric films, composite laminates or coextrusions of aforementioned films.

10. The dispenser of claim 9, wherein said wick comprises absorbent material selected from the group comprised of woven cotton fibers, nonwoven cotton fibers, woven synthetic fibers, nonwoven synthetic fibers, porous polymeric material, cellulose fibers, animal fibers, glass fibers, polymeric foam, and porous ceramics, wherein said absorbent wick material is capable of conveying said pharmaceutical liquid by capillary action and wherein said tubular element is comprised of impermeable material selected from the group comprised of metals and polymers.

11. The dispenser of claim 10, wherein said pharmaceutical liquid is maintained in a compartment isolated from said wick prior to removal of said containment member, said containment member comprising removable male-female interlocking barrier strips dividing said liquid reservoir into two liquid-tight compartments, wherein said barrier strips exert a clamping pressure on each side of said liquid reservoir wall members interposed between said barrier strips, wherein said wall members are pinched together effectively isolating said pharmaceutical liquid from said wick prior to functional operation, and wherein removal of said barrier strips permit said pharmaceutical liquid to contact said wick to commence the functional operation of said dispenser.

12. The dispenser of claim 10, wherein said pharmaceutical liquid is maintained in a compartment isolated from said wick prior to removal of said containment member, said containment member comprising a rupturable barrier seal interposed between said liquid reservoir wall members, wherein said rupturable barrier seal effectively divides said liquid reservoir into two liquid-tight compartments, and wherein rupture of said barrier seal by external pressure applied against said liquid reservoir wall members permit said pharmaceutical liquid to contact said wick to commence the functional operation of said dispenser.

13. The dispenser of claim 10, wherein said pharmaceutical liquid is maintained in a compartment isolated from said wick prior to removal of said containment means, said containment means comprising a frangible impermeable sealed liquid container within said reservoir, wherein said frangible container contains said pharmaceutical liquid and whereby rupture of said frangible container by external pressure applied against said reservoir container wall members permit said pharmaceutical liquid to contact said wick to commence functional operation of said dispenser.

14. A liquid dispensing device containing a supply of vegetative nutrients in liquid form stored in a liquid reservoir, which maintains said vegetative nutrient supply in isolation from the ambient atmosphere, whereby during functional operation, an absorbent wick forming part of a wick assembly makes contact with said vegetative nutrient liquid whereby said wick conveys by capillary action said vegetative nutrient liquid at a slow substantially constant rate to the opposite end of said wick to a diffusing emanator remote from said liquid reservoir, wherein said emanator diffuses said vegetative nutrient liquid into the soil of vegetative cultivations wherein:

A. said liquid reservoir comprises a generally planar bag formed by the peripheral union of two wall members, said wall members being comprised of impermeable flexible polymeric film material and being sealed together in a continuous manner along their edgewise periphery providing a liquid-tight peripheral seal wherein a passageway extends through said peripheral seal to accommodate the protrusion of said wick assembly between said wall members, wherein a liquid-tight seal is additionally maintained between said periphery seal and said wick assembly;

B. said wick assembly extending in a continuous manner from said liquid reservoir container to the emanator and making physical contact with said vegetative nutrient liquid supply during functional operation, and wherein said wick assembly comprises said absorbent wick laterally enclosed within a hollow impermeable tubular element, wherein said tubular element is open at each end allowing a portion of said wick to extend beyond said tubular element at each end, and wherein said wick makes physical contact with a diffusing surface of said emanator at one end, and during functional operation said wick on the other end makes physical contact with said vegetative nutrient liquid in said reservoir; said emanator as the diffusing element of said dispenser, comprising the end of said wick remote from said reservoir;

D. said vegetative nutrient liquid supply being maintained isolated from said wick prior to functional operation by means of a containment member, whereby upon removal of said containment member said vegetative nutrient liquid supply is free to contact said wick, thus commencing the functional operation of said dispensing device.

15. The dispenser of claim 14, wherein said liquid reservoir comprises said impermeable flexible polymeric film material selected from the group comprised of polyethylenes, polypropylenes, polyvinyl chlorides, polyacrylates, polyamides, polyesters, polycarbonates, polyvinylidene chlorides, ethylene vinyl acetates, polystyrenes, modified polystyrenes, polyfluorocarbons, metallized polymeric films, composite laminates or co-extrusions of aforementioned films.

16. The dispenser of claim 15, wherein said wick comprises absorbent material selected from the group comprised of woven cotton fibers, nonwoven cotton fibers, woven synthetic fibers nonwoven synthetic fibers, porous polymeric material, cellulose fibers, animal fibers, glass fibers, polymeric foam, and porous ceramics, wherein said absorbent wick material is capable of conveying said vegetative nutrient liquid by capillary action and wherein said tubular element is comprised of impermeable material selected from the group comprised of metals and polymers.

17. The dispenser of claim 16, wherein said vegetative nutrient liquid is maintained in a compartment isolated from said wick prior to removal of said containment member, said containment member comprising removable male-female interlocking barrier strips dividing said liquid reservoir into two liquid-tight compartments, wherein said barrier strips exert a clamping pressure on each side of said liquid reservoir wall members interposed between said barrier strips, wherein said wall members are pinched together effectively isolating said vegetative nutrient liquid from said wick prior to functional operation, and wherein removal of said barrier strips permit said vegetative nutrient liquid to contact said wick to commence the functional operation of said dispenser.

18. The dispenser of claim 16, wherein said vegetative nutrient liquid is maintained in a compartment isolated from said wick prior to removal of said containment member, said containment member comprising a rupturable barrier seal interposed between said liquid reservoir wall members, wherein said rupturable barrier seal effectively divides said liquid reservoir into two liquid-tight compartments, and wherein rupture of said barrier seal by external pressure applied against said liquid reservoir wall members permit said vegetative nutrient liquid to contact said wick to commence the functional operation of said dispenser.

19. The dispenser of claim 16, wherein said vegetative nutrient liquid is maintained in a compartment isolated from said wick prior to removal of said containment member, said containment member comprising a frangible impermeable sealed liquid container within said reservoir container, wherein said frangible container contains said vegetative nutrient liquid and whereby rupture of said frangible container by external pressure applied against said reservoir wall members permit said vegetative nutrient liquid to contact said wick to commence functional operation of said dispenser.

20. The dispenser of claim 16, wherein said emanator is adapted to permit protrusion beneath the surface of vegetative cultivation soil with the aid of a hollow perforated tubular spike, wherein said hollow tubular spike permits the placement of a portion of said wick assembly into a central hollow channel of said spike, and wherein a lip is located on the top of said spike to aid in pushing said spike beneath soil surface, wherein said spike is also pointed on the bottom, and wherein perforations through said spike permit the diffusion of said vegetative nutrient liquid from the emanator into the soil.

* * * * *